United States Patent
Zettler et al.

(10) Patent No.: US 10,229,805 B2
(45) Date of Patent: Mar. 12, 2019

(54) DETECTION OF DEPENDENT FAILURES

(71) Applicant: Infineon Technologies AG, Neubiberg (DE)

(72) Inventors: Thomas Zettler, Hoehenkirchen-Siegertsbrunn (DE); Kirk Herfurth, Munich (DE)

(73) Assignee: Infineon Technologies AG, Neubiberg (DE)

( * ) Notice: Subject to any disclaimer, the term of this patent is extended or adjusted under 35 U.S.C. 154(b) by 34 days.

(21) Appl. No.: 15/240,544

(22) Filed: Aug. 18, 2016

(65) Prior Publication Data

US 2016/0365213 A1 Dec. 15, 2016

Related U.S. Application Data

(63) Continuation of application No. PCT/EP2014/053214, filed on Feb. 9, 2014.

(51) Int. Cl.
| | |
|---|---|
| G01L 1/00 | (2006.01) |
| G01T 1/00 | (2006.01) |
| G01K 13/00 | (2006.01) |
| G01R 29/08 | (2006.01) |
| H01H 71/12 | (2006.01) |
| H01H 35/00 | (2006.01) |
| H01H 83/00 | (2006.01) |
| G01R 31/28 | (2006.01) |
| G01N 27/22 | (2006.01) |

(52) U.S. Cl.
CPC .......... *H01H 71/125* (2013.01); *G01K 13/00* (2013.01); *G01L 1/00* (2013.01); *G01N 27/223* (2013.01); *G01R 29/0878* (2013.01); *G01R 31/2829* (2013.01); *G01T 1/00* (2013.01)

(58) Field of Classification Search
CPC ........ H01H 71/125; G01K 13/00; G01L 1/00; G01N 27/223; G01R 29/0878; G01R 31/2829; G01T 1/00
USPC .......................................... 307/116
See application file for complete search history.

(56) References Cited

U.S. PATENT DOCUMENTS

| | | | |
|---|---|---|---|
| 5,394,409 A | 2/1995 | Barthel et al. | |
| 6,453,433 B1 | 9/2002 | Vollrath | |
| 6,469,525 B2 * | 10/2002 | Baiardo | G01N 27/223 |
| | | | 324/667 |
| 9,568,969 B2 | 2/2017 | Yamanaka | |
| 2007/0011288 A1 | 1/2007 | Cases et al. | |

(Continued)

FOREIGN PATENT DOCUMENTS

| | | |
|---|---|---|
| CN | 1851491 A | 10/2006 |
| DE | 102 49 846 A1 | 5/2004 |

(Continued)

OTHER PUBLICATIONS

International Search Report dated Jan. 29, 2015 in connection with International Patent Application No. PCT/EP2014/053214.

*Primary Examiner* — Hal Kaplan
(74) *Attorney, Agent, or Firm* — Eschweiler & Potashnik, LLC

(57) ABSTRACT

Devices and methods are provided which facilitate detecting of a disturbance parameter being outside a predetermined range. Such disturbance parameter may for example cause dependent failures in redundant circuits, for example redundant circuits being arranged on a same substrate.

25 Claims, 11 Drawing Sheets

(56) References Cited

U.S. PATENT DOCUMENTS

| | | | |
|---|---|---|---|
| 2007/0194895 A1* | 8/2007 | Apostolopoulos | ............................ B60C 23/0428 340/447 |
| 2009/0140745 A1* | 6/2009 | Williams | ........... G01R 31/2829 324/522 |
| 2011/0153277 A1 | 6/2011 | Morath | |
| 2013/0004811 A1* | 1/2013 | Banerjee | .................. G01K 7/16 429/62 |

FOREIGN PATENT DOCUMENTS

| | | |
|---|---|---|
| JP | H01259251 A | 10/1989 |
| JP | H07320453 A | 12/1995 |
| JP | 2000100056 A | 4/2000 |
| JP | 2006246558 A | 9/2006 |
| JP | 2007221880 A | 8/2007 |
| JP | 2013196626 A | 9/2013 |
| WO | 00/57147 A1 | 9/2000 |

\* cited by examiner $$U_a = (U_{e2} - U_{e1}) \cdot \frac{R4}{R3}$$

DETECTION OF DEPENDENT FAILURES

REFERENCE TO RELATED APPLICATION

This application is a continuation of PCT/EP2014/053214 filed on Feb. 19, 2014, the contents of which are incorporated by reference in their entirety.

FIELD

The present application relates to providing the possibility to detect dependent failures affecting for example two or more redundant circuits.

BACKGROUND

The use of electronic systems in safety critical environments, for example in automotive applications for driver assist systems and autonomous driving, requires a reliable operation of such electronic systems in order to avoid risks for persons depending on the operation of the electronic systems, for example passengers or other persons in case of automotive applications.

To increase safety, a measure often taken is to provide redundant circuits, i.e. to provide two or more circuits essentially performing the same function. When one of the redundant circuits fails, the other redundant circuit(s) is (are) still available. Moreover, failure of one of the redundant circuits is usually easily detectable as in case for example one of two redundant circuits fails, the output signals of the two redundant circuits will differ from each other. Another approach is to provide a first circuit to perform a certain function and a second circuit to monitor correct operation of the first circuit.

However, there is a kind of failures referred to also as dependent failures, which may lead to a simultaneous malfunction or failure of two redundant circuits, or may lead to a simultaneous failure of a first circuit to perform a certain function and a second circuit monitoring the first circuit. These dependent failures may in particular occur in cases where two or more redundant or otherwise related circuits are provided on a single substrate, for example integrated on a single substrate, as in this case the circuits are located close to each other, and are coupled via the substrate.

DETAILED DESCRIPTION

Figure 1:
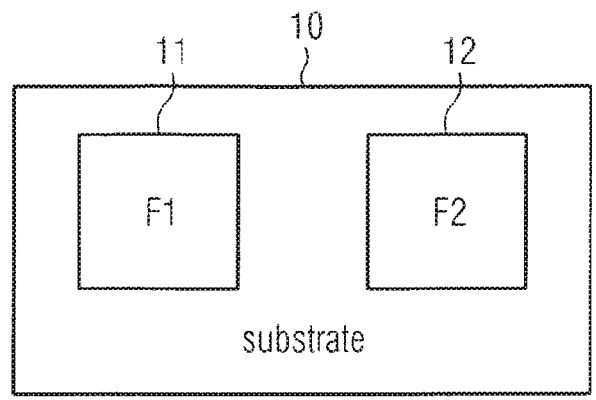
FIG. 1 is a schematic diagram of a circuit according to an embodiment.

In the following, various embodiments will be described in detail referring to the attached drawings. It is to be noted that these embodiments are not to be construed as limiting the scope of the present application in any way, but are merely given as illustrative examples. For instance, describing an embodiment with a plurality of elements is not to be construed as indicating that all these elements are necessary for implementing embodiments, as in other embodiments some of these features may be omitted, or may be replaced by alternative elements. Furthermore, elements from different embodiments may be combined to generate further embodiments unless specifically noted otherwise.

Some of the embodiments may comprise redundant circuits. Redundant in this respect may indicate that the circuits are designed to perform the same or an equivalent function. The redundant circuits may be parts of a single circuit, for example a single integrated circuit on a substrate. Generally, in the context of the present application, the term "circuit" may also be used to refer to only part of a circuit. In other words, a circuit may be formed of several circuit parts, and these circuit parts may also be simply referred to as circuits. For example, two or more circuits may be integrated together on a substrate in a single integrated circuit. To provide the same or equivalent functionality, in some embodiments the circuits may be nominally identical, for example the same circuit layout being used for both circuits. "Nominally" in this context indicates that deviations may still exist for example due to manufacturing or other tolerances. In other embodiments, the functionally equivalent circuits may have different circuit designs to perform the same function. For example, if the desired function is an analog-to-digital conversion, one circuit may be a first type of analog-to-digital converter (for example flash analog-to-digital converter), and the other circuit may be a second type of analog-to-digital converter (for example sigma-delta analog-to-digital converter).

Various disturbance parameters may act on circuits. A disturbance parameter generally in the context of the present application may refer to a parameter which may affect the functioning of a circuit. For example, the behavior of a circuit may depend on the temperature the circuit is at, the temperature in this case being an example for a disturbance parameter. Further examples for disturbance parameters will be explained further below. A circuit usually may be specified to work in a certain range of a disturbance parameter, but correct functioning may not be guaranteed outside this range. In many cases, the specified range for a disturbance parameter may depend on the application of the circuit. For example, circuits used at or near a combustion engine of an automotive vehicle are generally required to operate reliably over a wide range of temperatures, whereas circuits operating in a comparatively temperature stable environment, for example indoors, may have a comparatively narrow specified range.

Redundancy may be used to enhance functional safety. Functional safety of electronic systems may be specified in various standards or norms. For example, requirements for functional safety of electronic systems in passenger cars are specified in ISO 26262. The term "functional safety" is defined in ISO 26262, Part 1, 1.5.1 as "absence of unreasonable risk due to hazards caused by malfunctioning behavior of electrical or electronical systems" and is used in this sense in the present application.

According to some embodiments, a dependency breaking circuit may be provided, comprising a sensing element sensitive to at least one disturbance parameter, and an output coupled with the sensing element, a signal at the output being dependent on the at least one disturbance parameter in a well-defined manner. Well-defined manner in this respect indicated that by monitoring the output, the at least one disturbance parameter may be monitored, in particular such that it can be detected if the at least one disturbance parameter is outside a specified range. In other words, a response of a signal at the output to the at least one disturbance parameter is well-defined. The term "response" may be used herein to describe a behavior of a signal, for example an output signal, depending on a parameter, for example a disturbance parameter. The well-defined manner may be chosen as needed for a particular application and in particular may be chosen such that it can be easily detected when the at least one disturbance parameter is outside the specified range, for example by providing a response that is easy to detect. Examples for such responses and well-defined manners will be given later in greater detail. Generally, a disturbance parameter describes an influence on a device which potentially may lead to a failure of the device. It is therefore of interest to provide means of detecting the disturbance parameter leaving the specified range for this disturbance parameter.

Such a dependency breaking circuit may in particular be used in safety applications, for example to detect so-called dependent failures. Such dependent failures may be caused by the at least one disturbance parameter leaving the specified range, as will be described later.

Some embodiments may comprise a first dependency breaking circuit as mentioned above and a second dependency breaking circuit as mentioned above. The well-defined manner in which the output is dependent on the at least one disturbance parameter may differ for the first and second circuit, for example by exhibiting different slopes or signal jumps in different directions when the at least one disturbance parameter leaves the specified range. In other words, responses of output signals of the first and second dependency breaking circuits differ in such embodiments, i.e. a first response of the signal at the output of the first dependency breaking circuit when the at least one disturbance parameter leaves a specified range differs from a second response of the signal at the output of the second dependency breaking circuit when the at least one disturbance parameter leaves the specified range.

In other embodiments, a functional safety device is provided, comprising a first circuit to provide a predetermined functionality, a second circuit to provide the predetermined functionality to provide redundancy, and a dependency breaking circuit as mentioned above, wherein the dependency breaking circuit is coupled with the first circuit to modify an output of the first circuit when the at least one disturbance parameter is outside a specified range. In such an embodiments, when the at least one disturbance parameter leaves the specified range, through the modification the signals output by the first and second circuits become distinct from each other. Therefore, in such embodiments it may be detected when the at least one disturbance parameter leaves the specified range by monitoring these signals.

In further embodiments, a functional safety device is provided, comprising a first circuit to provide a predetermined functionality when at least one disturbance parameter is within a specified range, and a second circuit to provide the predetermined functionality when the at least one disturbance parameter is within the specified range to provide redundancy, wherein the first circuit is detuned with respect to the second circuit to cause the first signal to deviate from the second signal by more than the predetermined tolerance when the at least one disturbance parameter is outside the specified range. In such embodiments, through the detuning it may be detected when the at least one disturbance parameter leaves the specified range by monitoring the first and second signals.

According to some other embodiments, a device is provided, comprising a first output and a second output. In an embodiment, within a specified range of a disturbance parameter a first signal at the first output corresponds to a second signal at the second output within a predetermined tolerance. Further, in an embodiment outside the specified range of the disturbance parameter the first signal deviates from the second signal by more than the predetermined tolerance. For example, a difference between the first signal and the second signal may increase with increasing distance of the disturbance parameter to the specified range.

In such an embodiment, it may therefore be detected that the disturbance parameter leaves the specified range, for example by comparing the first signal with the second signal.

In an embodiment, the first output may be an output of a first circuit, and the second output may be an output of a second circuit. In an embodiment, the first circuit and the second circuit may comprise redundant circuits, for example provide a predetermined functionality within the specified range of the disturbance parameter. In such embodiments, the first circuit and the second circuit are designed such that when the disturbance parameter leaves the specified range, their output signals deviate from each other, such that the leaving of the specified range may be detected. In some embodiments, the first and second circuits may be provided on a single substrate.

Such a device may for example be obtained by adding one or more additional structures responsive to the disturbance parameter leaving the specified range to otherwise functionally equivalent first and second circuits. For example, the first circuit and/or the second circuit may comprise a dependency breaking circuit as defined above. In other embodiments, elements of functionally equivalent first and second circuits may be modified such that their output signals differ outside the specified range.

According to another embodiment, a substrate may be provided, comprising a first circuit, a second circuit providing a safety mechanism for the first circuit, and a third circuit, an output signal of the third circuit being sensitive to a disturbance parameter being outside a specified range. For example, the third circuit may comprise a dependency breaking circuit as mentioned above.

In some embodiments, the second circuit may be nominally equivalent to the first circuit to provide redundancy. "Nominally equivalent" in this respect means that the first and second circuit are designed to perform the same function. In other embodiments, the second circuit may perform a monitoring function for the first circuit.

In some embodiments, by using the third circuit, it may be detected when a disturbance parameter is outside a specified range, which in some embodiments could adversely affect the functioning of the first and second circuits.

In other embodiments, a method is provided, comprising:

measuring a first signal at a first output of a circuit on a substrate, the circuit being sensitive to at least one disturbance parameter, measuring a second signal at a second output of the circuit, and deciding that the at least one disturbance parameter is outside a specified range, if a property of the first signal differs from the property of the second signal by more than a predetermined tolerance.

Turning now to the Figures, in FIG. 1 a circuit, for example redundant circuit, according to an embodiment is shown. The circuit of the embodiment of FIG. 1 comprises a first circuit 11 and a second circuit 12 arranged on a common substrate 10. First circuit 11 and second circuit 12 may be nominally equivalent, for example designed to perform essentially the same function.

As will be explained later on, first circuit 11 and second circuit 12 may be modified by adding specific additional circuits, also referred to as dependency breaking structures or dependency breaking circuits, or by modifying elements of the circuit such that outside a specified range of a disturbance parameter the behavior of first and second circuits 11, 12 differs from each other. In order to illustrate this further, next some circuit models used for illustration purposes will be discussed with reference to FIGS. 2 and 3.

Figure 2:
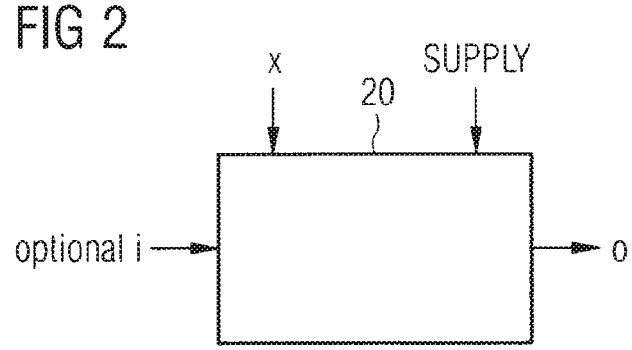
FIG. 2 is a block diagram illustrating a generic circuit according to an embodiment.

In FIG. 2 a simplified model 20 for a circuit or circuit like first circuit 11 or second circuit 12 are shown. Circuit 20 outputs a signal o. In some embodiments, circuit 20 may output signal o in response to an input signal i. In other cases, signal o may be output irrespective of any input signal i. It should be noted that the input signal i need not be an electrical signal, but may also be a different kind of signal, for example a magnetic field in case circuit 20 is a magnetic field sensor. It should be noted that circuit 20 is a simplified model, and in other circuits for example more than one input and/or more than one output may be provided. Furthermore, circuit 20 may have a supply terminal (denoted supply in FIG. 2) for receiving a supply voltage. x in FIG. 2 denotes one or more disturbance parameter(s) like temperature or other disturbance parameters as will be explained later. In the circuit of FIG. 1, for example via substrate 10, via ambient air or via other ambient gases disturbance parameter x may act both on first circuit 11 and second circuit 12. In conventional redundant circuits, an effect of the disturbance parameter may be difficult to detect when disturbance parameter x influences both first and second circuits 11, 12 in the same way. However, as will be explained in greater detail later in some embodiments measures are taken to make a disturbance parameter being outside a specified range detectable, in particular in a reliable manner.

Figure 3:
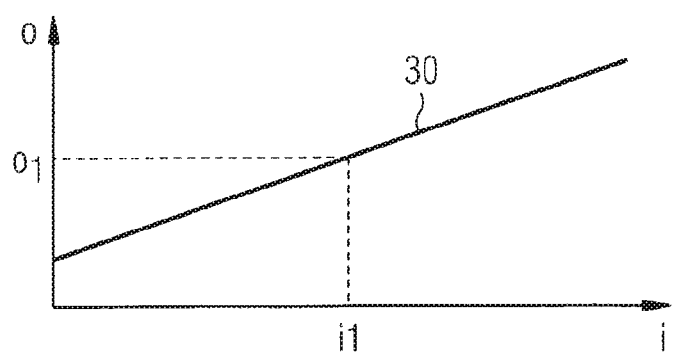
FIG. 3 is a diagram showing an example of a behavior of the circuit of FIG. 2.

In FIG. 3 an example behavior of the circuit model of FIG. 2 is shown. As shown in FIG. 3, the output value o changes depending on the input signal i as shown in linear function 30. For example, at an input signal having a value i1 an output signal having a value o1 is output. In examples without an input, a value o1 may be generally output, for example as a reference signal. As will be explained in the following, disturbance parameter x may influence the value o1 of the output signal.

As already mentioned, in the embodiment of FIG. 1 first circuit 11 and second circuit 12 may be designed such that errors or failures caused by disturbance parameter x may be detected, even if disturbance parameter x acts on both first and second circuits 11, 12.

Figure 4:
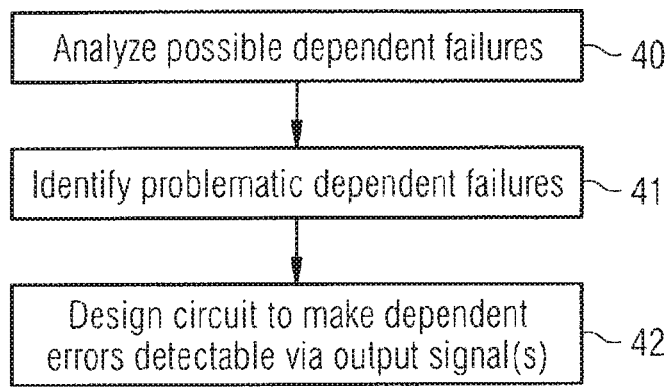
FIG. 4 is a flowchart illustrating a method according to an embodiment.

In FIG. 4, a method according to an embodiment usable for example for designing circuits like the circuit of the embodiment of FIG. 1 is shown. At 40, dependent failures which may possibly occur in a circuit are analyzed. Dependent failures in this respect may be failures which affect two or more redundant circuits, redundant circuits, or a first circuit performing a function and a second circuit monitoring the first circuit in the same or similar manner. Dependent failures may therefore be hard to detect. At 40, in some embodiments in particular dependent failures involving a coupling via a common substrate like substrate 10 of FIG. 1 and/or dependent failures which are more likely to occur when two redundant or otherwise related circuits are integrated on a same chip may be analyzed.

At 41, possibly problematic dependent failures are identified. In this respect, some of the dependent failures found by the analysis at 40 may not be problematic in a specific application and may therefore be disregarded. For example, for circuits which are intended to be employed in a temperature stable environment, dependent failures caused by huge temperature variations may not be an issue.

At 42, the circuit is designed to make dependent failures detectable via one or more output signals. For example, in the embodiment of FIG. 1 output signals of first and second circuits 11, 12 may become different from each other when one or more disturbance parameters associated with the dependent failures identified at 41 are outside a specified range.

Next, to illustrate this further various examples for dependent failures, for example dependent failures involving a coupling via a substrate, will be discussed. The examples discussed are not to be construed as limiting, and in other embodiments other kinds of dependent failures may be taken into account. Embodiments may be designed to take one or more types of dependent failures and/or associated disturbance parameters into account.

Dependent failures may include for example hardware failures, which may be caused by physical defects influencing e.g. two or more redundant circuits or a first circuit performing a function and a second circuit monitoring the first circuit. Another type of dependent failures are development faults, e.g. faults introduced within development and which may cause a dependent failure, e.g. due to crosstalk between redundant circuits, incorrect implementation of a functionality, specification errors or wrong microcontroller configuration.

Dependent failures may also include installation faults, e.g. faults introduced during installation which have a capability to cause a dependent failure, for example due to interference between adjacent parts of a circuit or device, or due to a faulty microcontroller PCB (printed circuit board) connection. Also, dependent failures may be caused by repairs which have the capability to cause dependent failures, for example faults in memory spare columns/rows due to faulty installation of memory components.

Dependent failures may also include failures of common, i.e. shared, internal and/or external resources. For example, for a microcontroller or also other digital circuits, shared resources may include clocks, reset and power supply, including their distribution. Therefore, for example inaccuracies in a shared clock signal may adversely affect functioning of two redundant circuits using this clock signal. Also, stress due to specific situations like wear or ageing, e.g. due to electromigration, may cause dependent failures. Finally, also environmental factors like the already mentioned temperature, electromagnetic interference (EMI), humidity, mechanical stress and the like may cause dependent failures.

A further cause for dependent failures may be radiation, for example particle radiation like α-particles. Such α-particles may stem from various sources, including chip housings. In some cases, such an α-particle may propagate in a substrate, e.g. semiconductor substrate, in a direction parallel to a plane of the substrate and thus may affect different circuits or circuit portions of the substrate, for example redundant circuits. This in turn may cause a dependent failure.

It is clear from the examples given above that dependent failures may stem from random failures and/or systematic failures. Random failures include for example hard errors, e.g. short circuits caused by defects, and/or transient errors like soft errors, for example a content of a memory cell being altered by particle radiation. Systematic failures may for example include development errors and/or software errors.

In the following, as non-limiting examples some kinds of disturbance parameters that may cause dependent failures will be discussed in more detail. In some cases, such dependent failures may be associated with or enhanced by a substrate like a semiconductor substrate on which e.g. two redundant circuits or a circuit and a monitoring circuit associated therewith are formed. Such dependent failures may e.g. occur in the circuit discussed with reference to FIG. 1 or at least some of the circuits discussed further below. Some examples for disturbance parameters causing such dependent failures which will be treated in some more detail below include temperature, electromagnetic interference, humidity, mechanical stress and electrical charges in the substrate.

Figure 5:
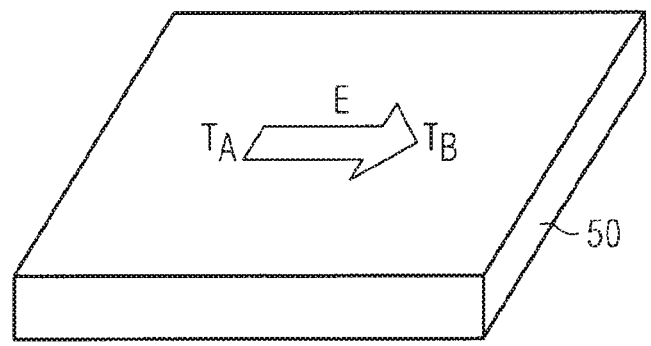
FIGS. 5-8 are schematic views illustrating different disturbing influences on a substrate.

In FIG. 5, as an example a substrate 50 with two temperatures $T_A$ and $T_B$ (i.e. a temperature gradient) is shown. A thermal energy flow E is caused by the temperature gradient which eventually leads to a balancing of the temperatures. In other words, different parts of substrate 50 (e.g. parts where redundant circuits like circuits 11 and 12 of FIG. 1 may be provided) are thermally coupled, and temperature changes in one part may also affect the other part. Therefore, a temperature being outside a specified range may lead to failure or erroneous behavior of a circuit in different parts of the substrate, such as circuits 11 or 12 of FIG. 1.

A change of temperature, for example a change of a temperature at pn junctions of semiconductor devices, may cause changes in current and operation range of semiconductor devices like transistors or diodes.

Figure 6:
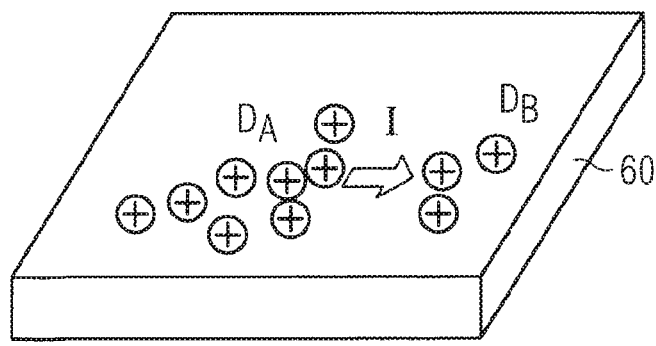

In FIG. 6, a substrate 60 with two different carrier densities (holes in the example shown, but also applicable to other carrier types like electrons) $D_A$, $D_B$ is shown. A current I leads to a balancing of the carrier densities. Therefore, somewhat similar to the thermal coupling discussed with reference to FIG. 5, in FIG. 6 an electric coupling between different parts of substrate 60 is present, and therefore carrier densities outside specified ranges may affect e.g. two redundant circuits in different parts of the substrate and therefore cause dependent failures.

Figure 8:
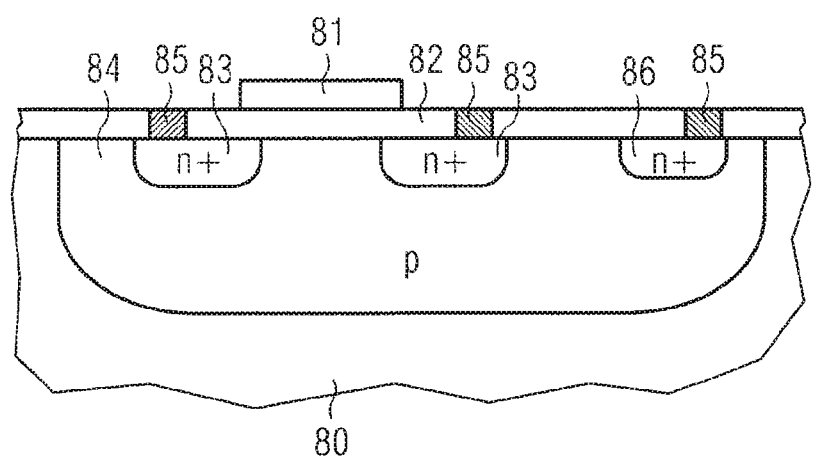

Effects of carriers in the substrate will be illustrated with reference to FIG. 8. In FIG. 8 a NMOS field effect transistor formed in a substrate 80 is shown. The NMOS transistor comprises a polysilicon gate 81, a gate insulator 82 (for example an oxide layer), two n+ doped source/drain regions 83 formed in a p-well 84, and an n+ doped well contact 86. Source/drain regions 83 and well contact 86 are contactable via respective metallic contacts 85, for example made of tungsten. In case for example p-well 84 is positively charged as indicated in FIG. 6 (high hole concentration), via the so-called back biasing effect this leads to a change in threshold voltage of the NMOS transistor and therefore also to a change in transistor current in some range of operation of the transistor, for example in a linear range. In other words, an effective resistance of the transistor may be modified by carriers in the substrate, which may cause an erroneous behavior of a circuit on the substrate comprising the transistor.

Figure 7:
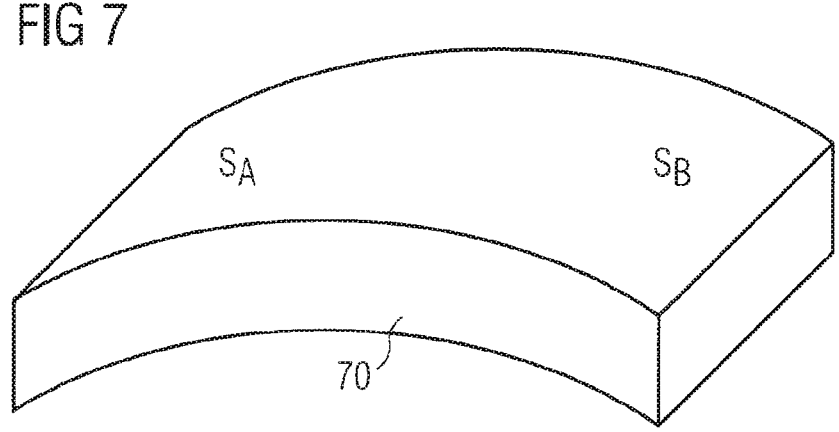

In FIG. 7, a substrate 70 with mechanical stress $S_A$ in a first part and mechanical stress $S_B$ (which may be equal to or different from $S_A$) in a second part of the substrate is shown. In many cases, if stress appears in one part of the substrate, stress also appears in other parts (for example due to a bending of the complete substrate), which may lead to dependent failures.

Mechanical stress may influence carrier mobility in the semiconductor substrate and/or in circuits formed on the substrate. This in turn may lead to changes in transistor currents.

As can be seen from the above explanations, the influence of various disturbance parameters may influence the behavior of electric circuits, for example transistor currents. This may for example lead to dependent failures in two redundant circuits, for example when the transistor currents are changed so much that reliable operation of the circuits is no longer guaranteed.

In particular, usually circuits are designed to operate properly as long as the disturbance parameters are within a certain specified range, while reliable operation is not guaranteed anymore when the disturbance parameters are outside the specified range.

In conventional approaches, for example even if the disturbance parameter is outside the specified range, two redundant circuits could still produce the same, albeit faulty, results. In contrast thereto, in some embodiments redundant circuits are modified to produce different results when a disturbance parameter is outside a specified range. In particular in some embodiments the redundant circuits may generate even diverging, complementary or opposite results when the disturbance parameter is outside the specified range. For example, circuits 11, 12 of the embodiment of FIG. 1 may be configured to produce, within a predetermined tolerance which may for example be due to manufacturing tolerances or acceptable tolerances for a specific application, the same results at an output o (for example output signal o1 for an input signal i1 as illustrated in FIG. 3) as long as a disturbance parameter is within a specified range. However, in embodiments outside the specified range the output signals may differ and may exhibit well-defined behavior, i.e. distinct responses, making it easy to detect that the disturbance parameter has left the specified range.

Figure 9A:
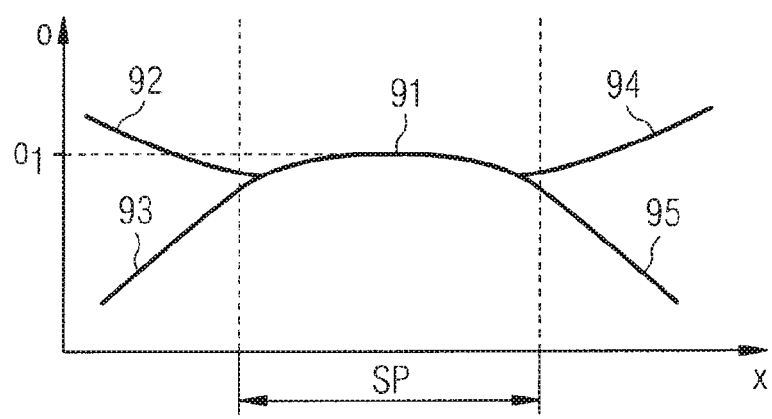
FIGS. 9A and 9B are diagrams illustrating the behavior of signals in some embodiments.
Figure 9B:
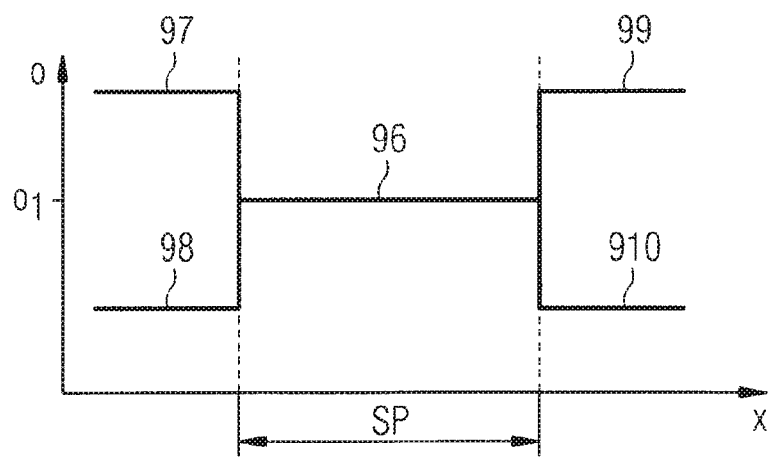

This is illustrated using a simple example in diagrams shown in FIGS. 9A and 9B. In FIG. 9A, a specified range of a disturbance parameter x (for example one of the disturbance parameters mentioned above like temperature, stress, humidity, carriers in a substrate or also electromagnetic interference) is marked with SP. Within this specified range SP, two circuits, for example two redundant circuits or two dependency breaking circuits, like circuits 11, 12 of FIG. 1 produce essentially the same output signal as illustrated by a curve part 91, for example output signal with a value $o_1$ as illustrated in FIG. 9A.

When the disturbance parameter x leaves the specified range SP, in embodiments the output signals from two circuits differ from each other. For example, circuit 11 of FIG. 1 may have a behavior as illustrated by curve parts 92 and 94 in FIG. 9A, and circuit 12 of FIG. 1 may have a behavior as illustrated by curve parts 93 and 95 in FIG. 9A, or vice versa. Other behaviors are also possible. For example in another embodiment curve parts 92 and 95 may correspond to the behavior of circuit 11 of FIG. 1, and curve portions 93 and 94 may correspond to the behavior of circuit 12 of FIG. 1, or vice versa.

In the example of FIG. 9, the difference between outputs of the two circuits (i.e. between curves 92 and 93 and between curve portions 94 and 95) increases as the distance between the disturbance parameter x and the specified range SP increases at least for a certain range of the disturbance parameter. In other embodiments, the behavior of the signals may differ from the behavior shown in FIG. 9A, as long as the signals from the two circuits are clearly distinguishable outside the specified range SP. For example, while in FIG. 9A the output signal of one of the circuits has a positive slope, while the output signal of the other circuit has a negative slope outside the specified range, in other embodiments the slopes for the curves for both circuits may have the same sign, but different magnitude (for example steep increase and slow increase, steep decline and slow decline etc.), or may in any other way be distinguishable, in particular clearly distinguishable so as to be surely able to detect the disturbance parameter leaving the specified range.

To give another example, FIG. 9B shows a further example of a behavior of two circuits according to some embodiments, for example circuits 11 and 12 of FIG. 1. In FIG. 9B, a specified range of a disturbance parameter x (for example one of the disturbance parameters mentioned above like temperature, stress, humidity, carriers in a substrate or also electromagnetic interference) is again marked with SP. Within this specified range SP, two circuits, for example two redundant circuits or two dependency breaking circuits, like circuits 11, 12 of FIG. 1 produce essentially the same output signal as illustrated by a curve part 96, for example output signal with a value $o_1$ as illustrated in FIG. 9B.

When the disturbance parameter x leaves the specified range SP, in embodiments the output signals from two circuits differ from each other. For example, circuit 11 of FIG. 1 may have a behavior as illustrated by curve parts 97 and 99 in FIG. 9B, and circuit 12 of FIG. 1 may have a behavior as illustrated by curve parts 98 and 910 in FIG. 9B, or vice versa. Other behaviors are also possible. For example in another embodiment curve parts 97 and 910 may correspond to the behavior of circuit 11 of FIG. 1, and curve portions 98 and 99 may correspond to the behavior of circuit 12 of FIG. 1, or vice versa. As can be seen, in contrast to slopes shown in FIG. 9A, in FIG. 9B upon leaving the specified range SP one of the signals output by the two circuits "jumps" towards a positive signal value, e.g. a positive voltage like a positive supply voltage, and the other one of the signals output by the two circuits "jumps" towards a negative signal value, e.g. a negative voltage like a negative supply voltage or ground.

Therefore, in such embodiments by comparing the output signals of the two circuits, it may be detected that the disturbance parameter x is outside the specified range SP. For example, it may be decided that the disturbance parameter is outside the specified range when a difference between the output signals is more than a predetermined tolerance. In some embodiments, to achieve this, the outputs of two redundant circuits may be modified by one or more dependency breaking structures, e.g. circuits, such that the outputs become clearly distinguishable when the disturbance parameter leaves the specified range.

In the example of FIGS. 9A and 9B, the signals may for example be voltage signals or current signals, and $o_1$ may then be a certain voltage value or current value. In other embodiments, other quantities of output signals may differ when a disturbance parameter leaves a specified range, for example frequency, duty cycle or pulse form, as long as by monitoring the output signals it can be detected when the disturbance parameter x leaves the specified range.

In FIGS. 9A and 9B, the specified range SP has a lower boundary and an upper boundary. In other cases only one boundary may be present. For example, some disturbance parameters may only be critical, e.g. likely to cause dependent failures, if they exceed some limit.

Next, various embodiments describing how for example a behavior as illustrated in FIG. 9A or 9B or any other behavior which makes it possible to detect a disturbance parameter being outside a specified range will be discussed in detail.

Figure 10:
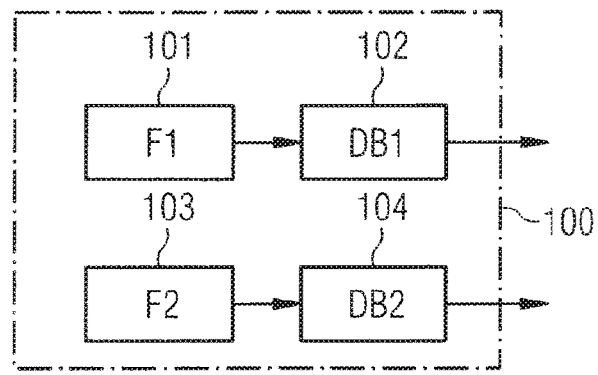
FIG. 10 is a block diagram of a circuit according to an embodiment.

In FIG. 10, a schematic block diagram of an embodiment is shown.

In the embodiment of FIG. 10, two circuits 101, 103 are provided on a substrate 100, for example a semiconductor substrate like a silicon substrate. First circuit 101 and second circuit 103 may be nominally equivalent circuits, i.e. they may be designed to perform the same function. For example, first circuit 101 and second circuit 103 may have identical circuit designs and may for example deviate from each other only due to manufacturing tolerances and similar effects.

First and second circuits 101, 103 may in some embodiments be used to perform safety critical functions, for example in an automotive environment, e.g. related to airbag deployment, automated breaking, autonomous driving or the like.

Furthermore, the embodiment of FIG. 10 comprises a first dependency breaking structure 102 coupled with an output of first circuit 101 and a second dependency breaking structure 104 coupled with an output of second circuit 103. A dependency breaking structure in the context of the present application generally refers to a circuit or circuit which is sensitive to a disturbance parameter, in particular to the disturbance parameter being outside a specified range. For example, in the embodiment of FIG. 10 first and second dependency breaking structures 102, 104 as long as a disturbance parameter is within a specified range may pass on output signals of first and second circuits 101, 103, respectively, essentially without modification. When the disturbance parameter is outside the specified range, dependency breaking structures 102, 104 modify signals output from first and second circuits 101, 103 so as to make them distinguishable from each other, for example to cause a behavior as explained with reference to FIG. 9A or 9B. In other words, the first and second dependency breaking structures 102, 104 in the embodiment of FIG. 10 modify the behavior of first and second circuits 101, 103, respectively, such that the behavior becomes clearly distinguishable when a disturbance parameter leaves a specified range. While for ease of representation "a" disturbance parameter is used for purposes of explanation, it should be noted that dependency breaking structures may be sensitive to more than one disturbance parameter, such that "a" in this context is to be understood as "at least one".

Specific examples for the implementation of dependency breaking structures will be given later in more detail.

It should be noted that in some embodiments first and second circuits 101, 103 and first and second dependency breaking structures 102, 104 may be integrated in a single circuit, and/or be provided on a single chip or substrate.

Figure 11:
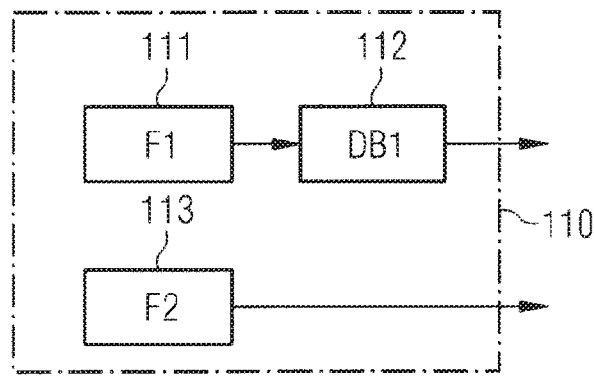
FIG. 11 is a block diagram of a circuit according to an embodiment.

In FIG. 11, a further embodiment is schematically illustrated. In the embodiment of FIG. 11, a first circuit 111 and a second circuit 113 are provided on a substrate 110. First and second circuits 111, 113 may be nominally equivalent circuits providing redundancy for safety critical applications. In some embodiments, first and second circuits 111, 113 as well as substrate 110 may correspond to first and second circuits 101, 103 and substrate 100 explained with respect to FIG. 10, and any explanations regarding these elements given with respect to FIG. 10 may also apply to the embodiment of FIG. 11.

In contrast to the embodiment of FIG. 10, the embodiment of FIG. 11 comprises only one dependency breaking structure 112 which modifies the output of first circuit 111. In embodiments, dependency breaking structure 112 may leave an output signal of first circuit 111 essentially unchanged as long as a disturbance parameter is within a specified range and may modify the output signal when the disturbance parameter leaves the specified range. In an alternative embodiment, dependency breaking structure 112 may modify the output of second circuit 113 instead of the output of first circuit 111. In other words, dependency breaking structure 112 in the embodiment of FIG. 11 modifies the behavior of either first or second circuit 111 or 113, such that the behavior of first and second circuits 111, 113 becomes clearly distinguishable when a disturbance parameter leaves a specified range.

Also in the embodiment of FIG. 11, through the modification introduced by dependency breaking structure 112 when the disturbance parameter is outside the specified range the output signal of second circuit 113 is distinguishable from the output signal of first circuit 111 as modified by dependency breaking structure 112. Therefore, a detection of the disturbance parameter being outside the specified range is made possible. It should be noted that in the embodiment of FIG. 10, through provision of two dependency breaking structures a difference between the output signal when the disturbance parameter is outside the specified range may be more pronounced and thus easier to detect than in case of the embodiment of FIG. 11, where only one dependency breaking structure 112 is provided. On the other hand, in some cases the embodiment of FIG. 11, by providing only one dependency breaking structure 112, may require less chip area and therefore may be cheaper to implement. Depending on the circumstances and requirements, any of the embodiments may be chosen.

In the embodiments of FIGS. 10 and 11, dependency breaking structures modify signals output from circuits which may for example perform safety critical functions. In other embodiments, dependency breaking structures may have separate outputs. Corresponding embodiments are for example shown in FIGS. 12 and 13.

Figure 12:
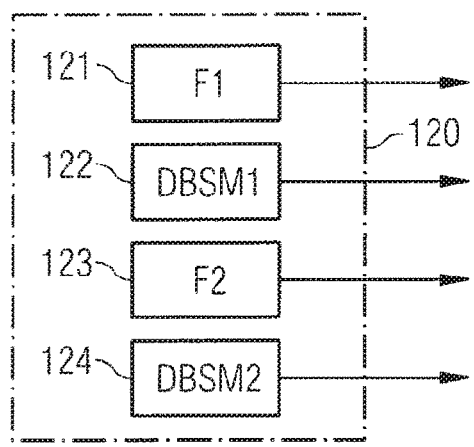
FIG. 12 is a block diagram of a circuit according to an embodiment.

In FIG. 12, first and second circuits 121, 123 are provided on a substrate 120. Similar to what has been explained already with respect to FIGS. 10 and 11, first and second circuits 121, 123 may provide redundant safety critical functions, i.e. they may have nominally equivalent functionality.

Additionally, two dependency breaking structures 122, 124 are provided on the substrate 120. In contrast to the embodiments of FIGS. 10 and 11, dependency breaking structures 122, 124 do not modify the output signal of circuits 121, 123, but their output signals are output individually. Otherwise, the functioning of dependency breaking structures 122, 124 may be similar to what was discussed with respect to FIGS. 10 and 11. In particular, they may output signals indicating that a disturbance parameter is outside a specified range and in particular may exhibit clearly different behaviors when the disturbance parameter is outside the specified range. For example an external evaluation circuit (not shown) may then evaluate the output signals of dependency breaking structures 122, 124 and issue a warning or take other appropriate measures when it is detected that the disturbance parameter is outside the specified range.

Figure 13:
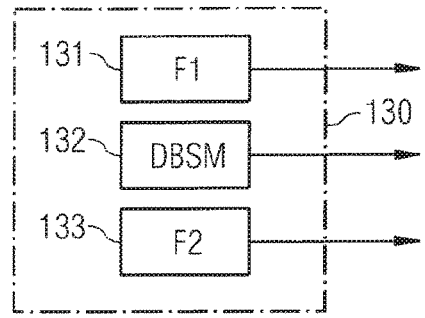
FIG. 13 is a block diagram of a circuit according to an embodiment.

A further embodiment is shown in FIG. 13. In the case of FIG. 13, two circuits 131, 133 are provided on a substrate 130; similar to what was explained for FIGS. 10-12. In particular, as has been explained previously first and second circuits 131, 133 may have nominally the same functionality to provide a redundancy, for example for safety critical functions, or may comprise a first circuit to perform a desired function and a second circuit to monitor correct functioning of the first circuit. In contrast to the embodiment of FIG. 12, only one dependency breaking structure 132 is provided on substrate 130, an output of which is tappable from outside substrate 130 and which may be evaluated to detect a disturbance parameter being outside a specified range. In other embodiments, more than two dependency breaking structures may be provided.

When for example packaged in a chip housing, embodiments like the embodiments of FIGS. 12 and 13 may require more pins than the embodiments of FIGS. 10 and 11, where no additional output for dependency breaking structures is needed. On the other hand, in the embodiments of FIGS. 12 and 13 there may be more freedom of design for the dependency breaking structures as they do not modify the output signals from first and second circuits which for example provide safety critical functions. Depending on circumstances and requirements, an appropriate embodiment may be chosen by a person skilled in the art.

The combination for example of circuit 101 with dependency breaking structure 102 in FIG. 4 is an example for circuit 11 of FIG. 1, and the combination of circuit 103 with dependency breaking structure 104 is an example for circuit 12 of FIG. 1.

Figure 14:
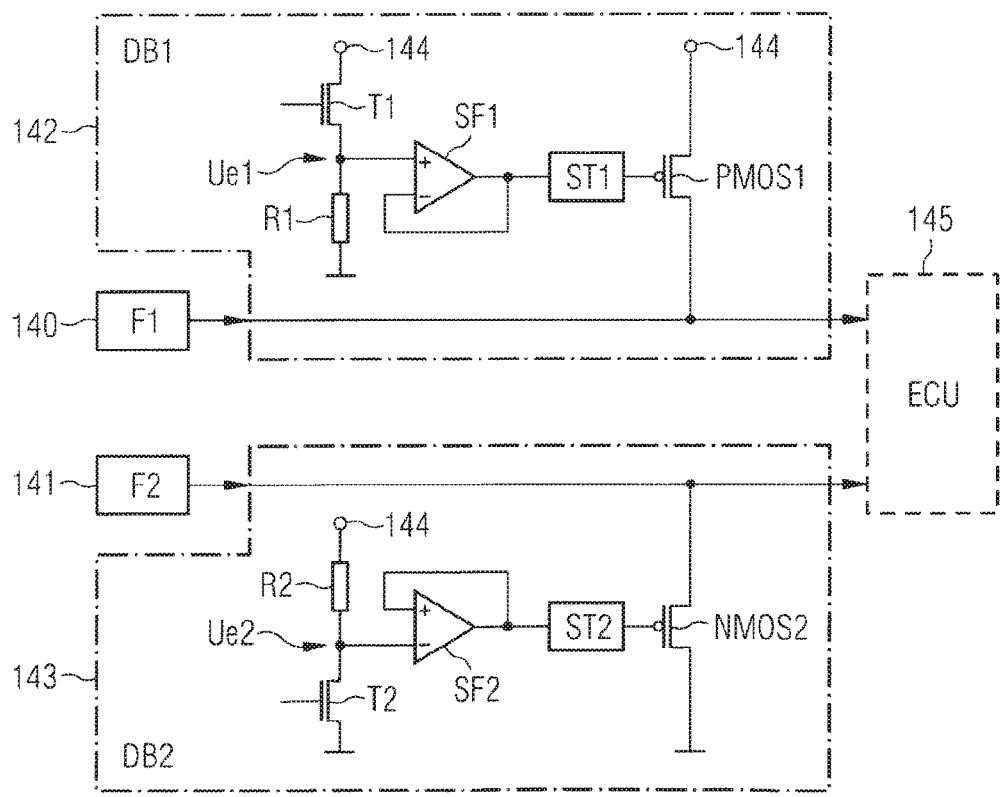
FIG. 14 is a diagram illustrating a circuit according to an embodiment.

In FIG. 14, an embodiment illustrating a possible implementation of dependency breaking structures is shown. The embodiment of FIG. 14 may be seen as an example implementation of the embodiment of FIG. 10 and comprises a first circuit 140 and a second circuit 141. First and second portions 140, 141 may be nominally equivalent, for example to provide redundancy for safety applications. A first dependency breaking structure 142 is associated with the first circuit 140, and a second dependency breaking structure 143 is associated with the second circuit 141.

Dependency breaking structure 142 comprises a voltage divider formed by a transistor T1 and a resistance R1 coupled for example between a positive supply voltage 144 and ground. This voltage divider outputs a voltage Ue1 at a node between transistor T1 and resistor R1. As discussed above, mechanical stress, carriers in the substrate or temperature variations may lead to a change of a behavior of transistor T1 like changes of transistor current or change of effective resistance. In other embodiments, other elements that have a variable impedance, e.g. resistance, depending on at least one disturbance parameter may be used, e.g. resistors. Therefore, as these disturbance parameters in the embodiment of FIG. 14 influence the behavior of transistor T1, depending on the disturbance parameters, the voltage Ue1 varies. Voltage Ue1 is fed to a voltage follower (unity gain buffer) SF1 which outputs voltage Ue1 decoupled from the voltage divider. An output of voltage follower SF1 is fed to a Schmitt trigger ST1. A Schmitt trigger, as known in the art, essentially has a switching behavior with a hysteresis, which is shown by a curve 150 in FIG. 15.

Figure 15:
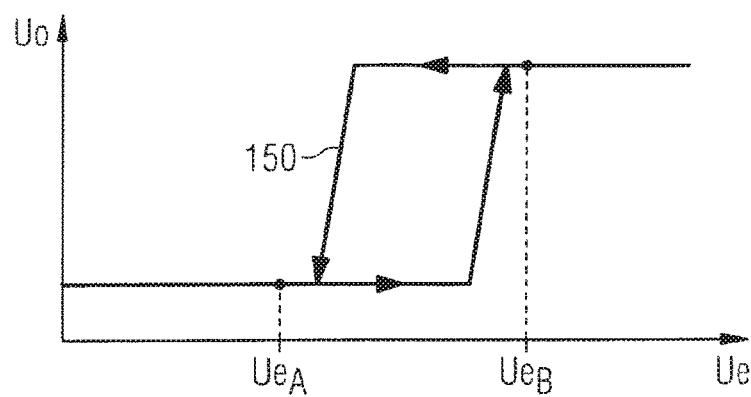
FIG. 15 is a diagram illustrating hysteresis behavior of a Schmitt trigger usable in some embodiments.

Let us assume a normal operation with one or more disturbance parameters each of which being within its specified range. The voltage fed to Schmitt trigger may in this case be for example $Ue_B$, as is depicted in FIG. 15, resulting in a logic high output signal of Schmitt trigger ST1, which is fed to a PMOS transistor PMOS1. When voltage Ue1 is at $Ue_B$ as shown in FIG. 15 and Schmitt trigger ST1 outputs a logic high signal, PMOS transistor PMOS1 has a blocking behavior and therefore decouples positive supply voltage 144 from the output of first circuit 140. When now for example a disturbance parameter x (e.g. temperature, mechanical stress or carriers in a substrate) reduces a transistor current of transistor T1, via resistor R1 the voltage Ue1 is pulled towards ground, i.e. to lower values. When voltage Ue1 reaches a value $Ue_A$ as depicted in FIG. 15, the output of Schmitt trigger ST1 switches to a logic low state, and PMOS transistor PMOS1 becomes conducting. This in turn couples positive supply voltage 144 with the output of first circuit 140. Therefore, the output of first circuit 140 is pulled towards a positive supply voltage, which may in some embodiments correspond to a behavior similar to curve portions 92, 94 in FIG. 9. In embodiments, the dimensioning of transistor T1 is chosen such that the voltage $Ue_A$ is reached for example when a disturbance parameter x leaves a specified range. One may therefore consider the Schmitt Trigger ST1 controlling the PMOS transistor. Through the use of Schmitt Trigger ST1 having a hysteresis (corresponding to two threshold values $Ue_A$ and $Ue_B$ for switching the output signal of Schmitt Trigger ST1), a quick successive toggling of the signal controlling the PMOS transistor in a case where Ue1 is near $Ue_A$ and $Ue_B$ may be avoided in some embodiments. Nevertheless, in other embodiments instead of Schmitt Trigger ST1 and instead of other Schmitt Triggers mentioned below elements with a single threshold value, for example simple comparators, may be used.

Therefore, while the disturbance parameter is within the specified range, in the embodiment of FIG. 14 an output signal of first circuit 140 is not or at least not significantly modified by dependency breaking structure 142, whereas outside the specified range it is pulled towards a positive supply voltage.

Second dependency breaking structure 143 is configured to some extent similar to first dependency breaking structure 142, but has an NMOS transistor NMOS2 coupled between an output of second circuit 141 and ground; acting as a pull-down transistor. Furthermore, a voltage divider in second dependency breaking structure 143 comprises a resistor R2 and a transistor T2 coupled between positive supply voltage 144 and ground. This voltage divider generates a voltage Ue2 which is fed to a voltage follower SF2 followed by a Schmitt trigger ST2 which controls transistor NMOS2. Therefore, in the voltage divider of second dependency breaking structure 143 the "order" of resistor and transistor between positive supply voltage 144 and ground is reversed compared to first dependency breaking structure 142.

Transistor T2 is for example designed such that voltage Ue2, as long as a disturbance parameter is within a specified range, is smaller than $Ue_B$ in FIG. 15, for example at or below $Ue_A$. Similar to what was explained for first dependency breaking structure 142, for example when the disturbance parameter is outside the specified range, a transistor current of T2 becomes smaller. In case of FIG. 14, because of the reversed order of transistor and resistor this leads to the voltage Ue2 increasing. When the voltage reaches $Ue_B$ in FIG. 15, an output of Schmitt trigger ST2 of second dependency breaking structure 143 of FIG. 14 becomes high, such that NMOS transistor NMOS2 becomes conducting and pulls an output of second circuit 141 towards ground. In other words, here the opposite effect (a pulling towards ground) is achieved compared with first dependency breaking structure 142, where a pulling towards a positive supply voltage is achieved when the disturbance parameter leaves a specified range. Therefore, an effect as illustrated in FIG. 9B may be achieved in some embodiments, i.e. when the disturbance parameter is outside the specified range, the output signals of the embodiment of FIG. 14 diverge from each other, one being pulled towards positive supply voltage 144 and the other being pulled towards ground. Therefore, a diverging behavior of the output signals as illustratively shown in FIG. 9B may be obtained. However, depending on the implementation the behavior may differ from the one shown in FIG. 9B.

While in the embodiment of FIG. 14 output signals are pulled toward a positive supply voltage and ground, respectively, in other embodiments generally the signals may be pulled towards two different signal levels. For example, in other embodiments a positive supply voltage and a negative supply voltage may be used as the two different signal levels instead of the positive supply voltage and ground of FIG. 14.

The output signals may then be evaluated by an external unit, for example by an electronic control unit (ECU) 145. In some embodiments, electronic control unit 145 may for example issue an alarm when the two output signals deviate by more than a predetermined tolerance indicating a disturbance parameter being outside a specified range. ECU 145 may be an entity separate from elements 140 to 143. For example, elements 140 to 143 may be integrated on a single chip (as was explained with respect to FIG. 1 or the embodiments of FIGS. 10-13), and ECU 145 may be provided separately therefrom. ECU 145 may for example be an ECU of an automobile or any other entity and may in some embodiments also evaluate and use the output signals to perform other functions while the disturbance parameter is within the specified range.

In the embodiment of FIG. 14, when designing dependency breaking structures 142, 143, for example by performing analog simulations it may be ensured that an influence of one or more disturbance parameter(s) to be detected on transistors T1, T2 is maximized, while the functioning of the remaining circuits of dependency breaking structures 142, 143 are as regards their functions largely independent from the disturbance parameter.

Figure 16:
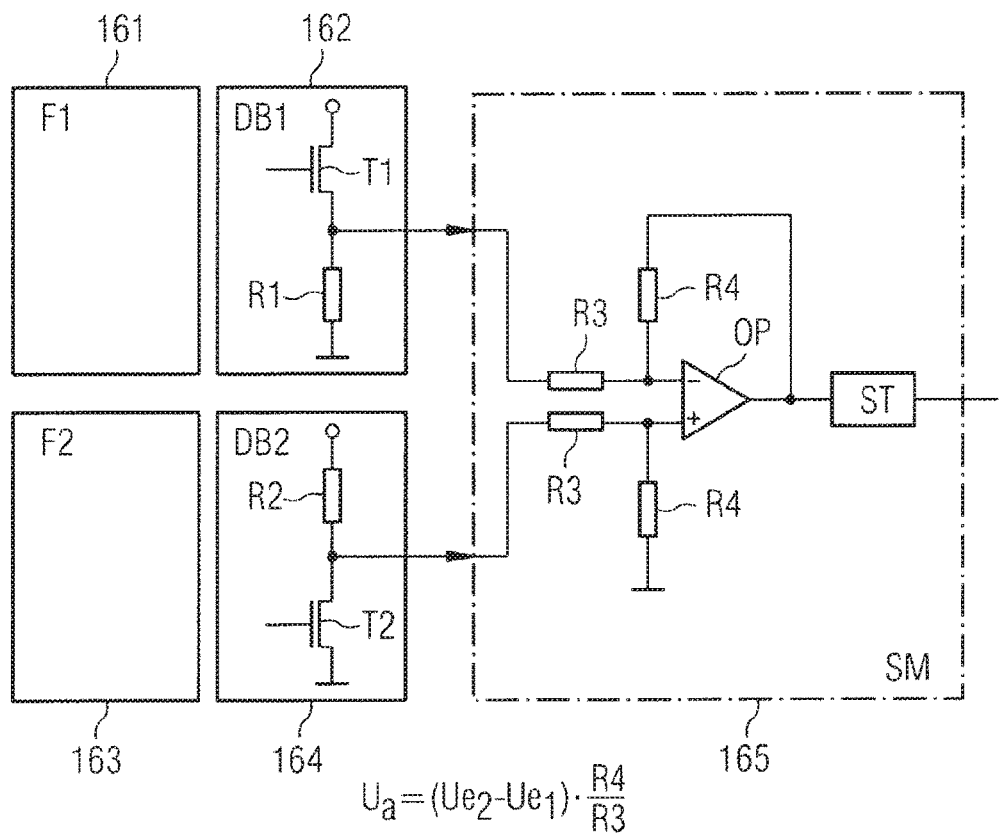
FIG. 16 is a diagram illustrating a circuit according to an embodiment.

In other embodiments, a circuit evaluating output signals of dependency breaking structures may be integrated together with circuits and dependency breaking structures. A corresponding embodiment is schematically shown in FIG. 16. In the embodiment of FIG. 16, again a first circuit 161 and a second circuit 163 are provided, which in embodiments may be functionally equivalent and may for example provide redundancy for a functionality of interest in safety functions, as explained previously. Furthermore, a first dependency breaking structure 162 and a second dependency breaking structure 164 are provided. In FIG. 16, outputs of first and second dependency breaking structures 162, 164 do not modify outputs of first and second circuits 161, 163, the embodiment of FIG. 16 in this respect being similar to the embodiment of FIG. 12. In other embodiments, they may modify the output of first and second circuits 161, 162, hence altering their functionality at least when a disturbance parameter is outside a specified range. First and second dependency breaking structures 161, 162 each comprise a voltage divider. The voltage divider of first dependency breaking structure 162 comprises a transistor T1 and a resistor R1 coupled between a positive supply voltage and ground. A voltage divider of second dependency breaking structure 164 comprises a resistor R2 and a transistor T2 coupled between a positive supply voltage and ground. In embodiments, these voltage dividers correspond to the voltage dividers of dependency breaking structures 142, 143 already described with reference to FIG. 14. Similar to the embodiment of FIG. 14, the dependency breaking structures 162, 164 may be sensitive to mechanical stress, temperature or carrier in the substrate and therefore monitor one or more disturbance parameter(s). In particular, as the order of resistor and transistor in second dependency breaking structure 164 is reversed compared to first dependency breaking structure 162, the responses of the first and second dependency breaking structures 162, 164 to a varying disturbance parameter have slopes with opposite signs, respectively (e.g. toward a positive supply voltage vs. towards ground).

In the embodiment of FIG. 16, the output signals from dependency breaking structures 162, 164 are fed to an evaluation circuit 165, which also may be referred to as a safety mechanism (SM). Evaluation circuit 165 may be integrated together with dependency breaking structures 162 and 164 and circuits 161 and 163 on a common substrate in some embodiments. In other embodiments, an evaluation circuit like evaluation circuit 165 may be provided in an external unit, for example ECU 145 of FIG. 14.

Evaluation circuit 165 comprises an operational amplifier OP. An output signal of first dependency breaking structure 162 is fed to a negative input of operational amplifier OP via a resistor R3, and an output signal of second dependency breaking structure 164 is fed to a positive input of operational amplifier OP via a further resistor R3. An output of operational amplifier OP is fed back to the negative input of operational amplifier OP via a feedback resistor R4, and the positive input of operational amplifier OP is coupled with ground via a further resistor R4.

The output of operational amplifier OP is further fed to a Schmitt trigger ST. An output voltage Ua of operational amplifier OP depends on an output voltage Ue1 of first dependency breaking structure 162 and an output signal Ue2 of second dependency breaking structure 164 as follows:

$$U_a = (Ue2 - Ue1) \cdot (R4/R3).$$

By designing Schmitt trigger ST accordingly, when the outputs of first and second dependency breaking structures 162, 164 differ by more than a threshold value, evaluation circuit 165 outputs for example a logic high value and otherwise a logic low value, or vice versa. It should be noted that the output signal of evaluation circuit 165 may be used directly as an indicator that a disturbance parameter is outside a specified range. In such an embodiment elements 162, 164 and 165 together may be used as dependency breaking structure 132 of the embodiment of FIG. 13. It should be noted that in alternative embodiments, an output of evaluation circuit 165 may be used to modify the output of either first circuit 161 or second circuit 163. In such an alternative embodiment, elements 162, 164 and 165 together may be used as dependency breaking structure 112 of the embodiment of FIG. 11.

Figure 17:
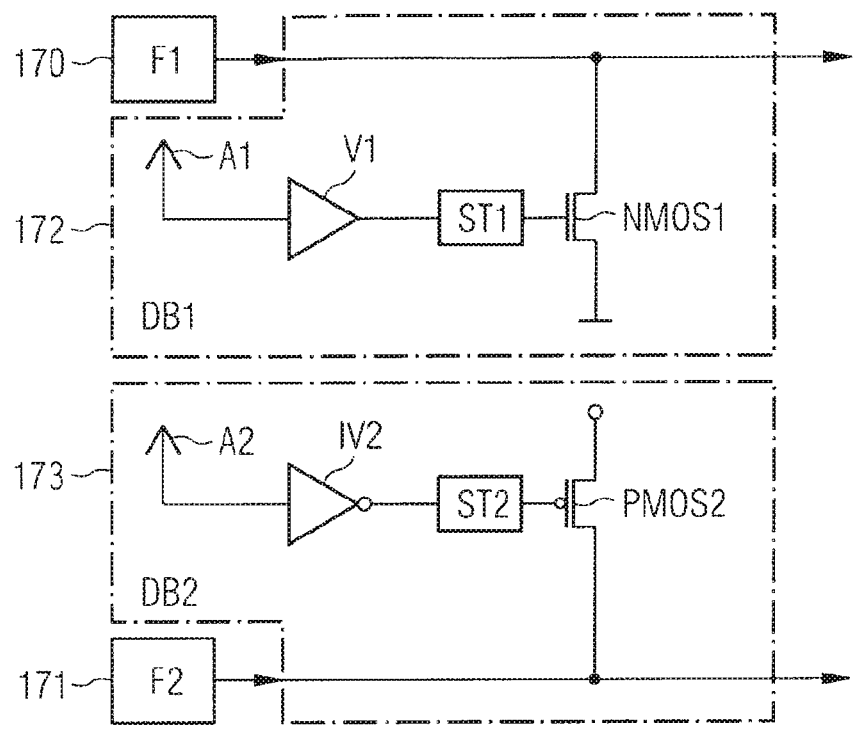
FIG. 17 is a diagram illustrating a circuit according to an embodiment.

A further embodiment is shown in FIG. 17. The embodiment of FIG. 17 is sensitive to electromagnetic radiation as a disturbance parameter, for example electromagnetic interference (EMI). The embodiment of FIG. 17 may be implemented on a substrate in a single chip. In the embodiment of FIG. 17, a first circuit 170 and a second circuit 171 are provided which may be functionally equivalent and may for example provide redundancy for safety applications. Furthermore, a first dependency breaking structure 172 is associated with first circuit 170, and a second dependency breaking structure 173 is associated with second circuit 171. First dependency breaking structure 172 is configured to modify an output of first circuit 170 when a disturbance parameter (e.g. electromagnetic radiation) leaves a specified range, in particular to pull the output of first circuit 170 towards ground, and second dependency breaking structure 173 is configured to modify the output of second circuit 171, for example pull the output of second circuit 171 towards a positive supply voltage, when the disturbance parameter (e.g. electromagnetic radiation) is outside a specified range.

First dependency breaking structure 172 comprises an antenna A1 to receive electromagnetic radiation followed by an amplifier V1. An output of amplifier V1 is fed to a Schmitt trigger ST1. An output of Schmitt trigger ST1 controls an NMOS transistor NMOS1. As long as electromagnetic radiation received by antenna A1 is below a threshold, Schmitt trigger ST1 for example outputs a logic low value (for example, a voltage output by V1 is below a voltage $Ue_B$ of FIG. 15), such that transistor NMOS1 is non-conducting. When the electromagnetic radiation rises, an output of amplifier V1 increases, until Schmitt trigger ST1 switches to a logic high output voltage making transistor NMOS1 conducting, therefore pulling the output of first circuit 170 towards ground.

Second dependency breaking structure 173 is configured similarly to first dependency breaking structure 172 and comprises an antenna A2 and a Schmitt trigger ST2. Instead of amplifier V1, an inverting amplifier IV2 is provided. Therefore, if electromagnetic radiation increases, a voltage output by inverting amplifier IV2 decreases. Furthermore, instead of an NMOS transistor, dependency breaking structure 173 comprises a PMOS transistor PMOS2 coupled between the output of second circuit 171 and a positive supply voltage. Therefore, in case of the second dependency breaking structure 173, when the radiation exceeds a threshold, transistor PMOS2 becomes conducting, and the output of second circuit 171 is pulled towards a positive supply voltage. Therefore, using dependency breaking structures 172, 173 when the disturbance parameter (electromagnetic radiation in this case) leaves the specified range, the output signals output by the embodiment of FIG. 17 will diverge from each other, for example similar to the behavior shown in FIG. 9. Evaluation of these signals may be performed as explained for example with reference to FIG. 14 or as explained with reference to FIG. 16, e.g. by external or internal evaluation circuits.

Figure 18:
FIG. 18 is a diagram illustrating a capacitance usable in some embodiments.

Next, embodiments which are able to take humidity as a disturbance parameter into account will be described with reference to FIGS. 18-22. In some embodiments, capacitances may be used to detect humidity. A first embodiment of a suitable capacitor is shown in FIG. 18. The capacitor of FIG. 18 comprises a first electrode 180 and a second electrode 181 with gas (like air) or vacuum in-between. Electrodes 180, 181 may for example be manufactured by a micro-mechanical processing, for example by corresponding etching of a silicon substrate. When humidity, for example water ($H_2O$) or other liquids enter the gap between first and second electrodes 180, 181, this changes a capacitance value of the capacitor of FIG. 18. As will be explained later with reference to FIGS. 20 and 21, this change in capacity may be used to detect humidity as a disturbance parameter. To achieve this, the capacitor of FIG. 18 may be integrated within a circuit, for example within a dependency breaking circuit as will be discussed later with reference to FIGS. 20 and 21.

Figure 19:
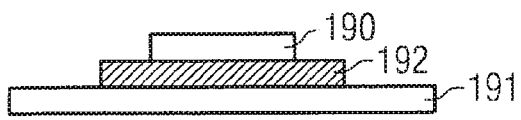
FIG. 19 is a diagram illustrating a capacitance usable in some embodiments.

A further embodiment of a capacitor usable to detect humidity is shown in FIG. 19. The capacitor of FIG. 19 comprises first and second electrodes 190, 191 with a dielectric material 192 provided between first and second electrodes 190, 191. The structure of FIG. 19 may for example be provided by a semiconductor process, for example by subsequent deposition of second electrode 191, dielectric material 192 and first electrode 190. When humidity, for example water ($H_2O$) or another liquid enters the dielectric material 192, a capacitance value of the structure of FIG. 19, i.e. a capacitance between first electrode 190 and second electrode 191, changes. In some embodiments, a dielectric material may be chosen where humidity can easily enter, for example a dielectric material having a certain porosity or a hygroscopic dielectric material absorbing humidity.

Figure 20A:
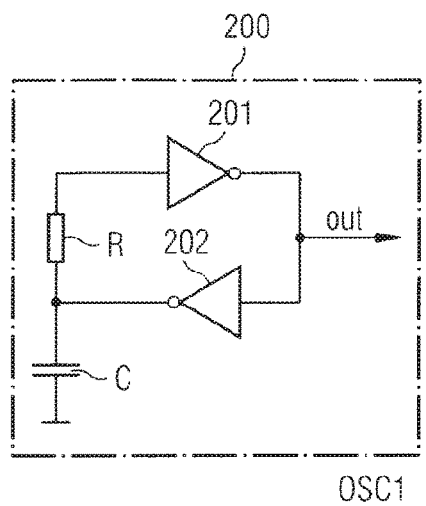
FIGS. 20A and 20B are diagrams illustrating oscillator circuits usable in some embodiments.

In FIG. 20A, an oscillator circuit 200, also labeled OSC1, is shown which comprises a capacitor C. Capacitor C may be implemented as explained with reference to FIGS. 18 and 19, i.e. be configured to change its capacitance value depending on a humidity. The oscillator circuit 200 further comprises a resistor R as well as two inverters 201, 202 coupled as shown in FIG. 20. In the oscillator circuit of FIG. 20A, when the capacitance C increases, a frequency at an output out decreases.

Figure 20B:
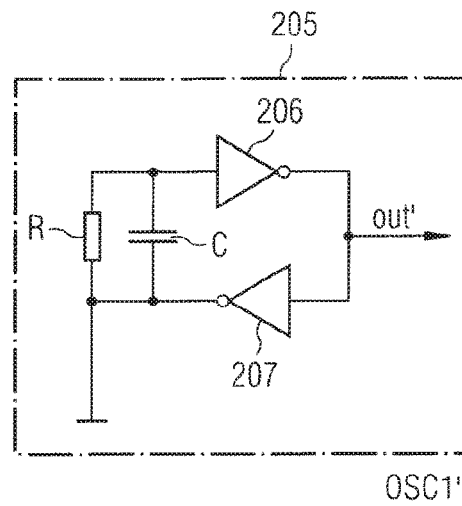

In FIG. 20B, an alternative oscillator circuit 205, also labeled OSC1' is shown which also comprises a capacitor C. Capacitor C again may be implemented as explained with reference to FIGS. 18 and 19, i.e. be configured to change its capacitance value depending on a humidity. The oscillator circuit 205 further comprises a resistor R. In contrast to FIG. 20A, in the embodiment of FIG. 20B capacitor C is coupled parallel to resistor R. Further, oscillator circuit 205 comprises two inverters 206, 207 coupled as shown in FIG. 20. In the oscillator circuit of FIG. 20A, when the capacitance C increases, a frequency at an output out increases, i.e. the behavior is the opposite to the behavior of oscillator circuit 200 of FIG. 20A. A person of ordinary skill in the art will readily appreciate alternate ways of implementing the opposite behavior of oscillator circuits as explained with regards to FIGS. 20A and 20B.

Figure 21:
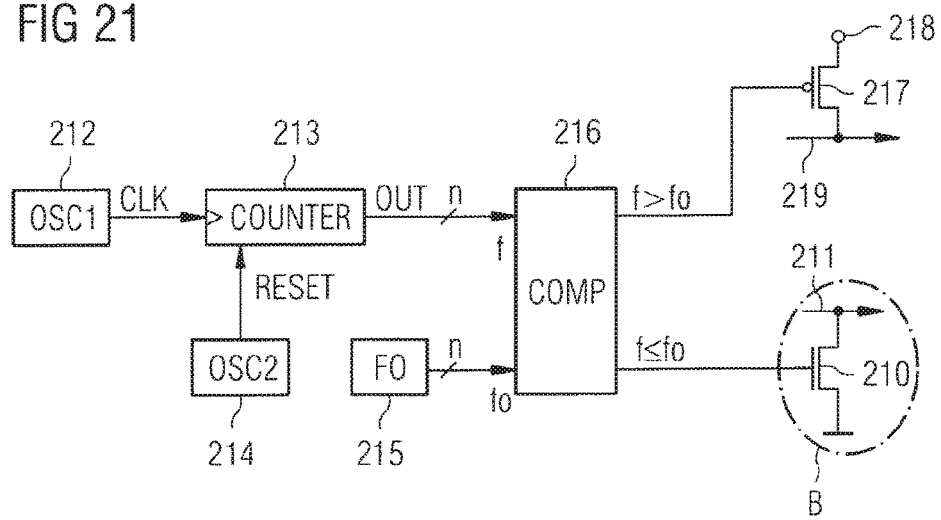
FIG. 21 is a dependency breaking circuit according to an embodiment.

This behavior of the oscillator circuits of FIGS. 20A and/or 20B may be used to implement a dependency breaking structure as shown in FIG. 21. The embodiment of FIG. 21 comprises a first oscillator 212 which may be implemented as explained with reference to FIG. 20A. In other words, first oscillator 212 has an output frequency which depends on a level of humidity.

An output of first oscillator 212 is fed to a clock input of a counter 213, which for example increases its output signal with each falling edge, each rising edge or both each falling and rising edges of a signal output by first oscillator 212. An output signal of counter 213 may be a digital n-bit signal, as illustrated in FIG. 21.

Furthermore, in the embodiment of FIG. 21, counter 213 comprises a reset input via which the counting may be reset, for example reset to zero. A signal of a second oscillator 214 is fed to the reset input of counter 213. Second oscillator 214 may operate at a fixed frequency which is smaller than the frequency of first oscillator 212, for example by at least one order of magnitude smaller.

In such an arrangement, the n-bit output signal of counter 213 is indicative of, for example proportional to, a frequency f of the output signal of first oscillator 212. This output signal is fed to a first input of a comparator 216. Furthermore, a fixed value representing a threshold frequency $f_0$ is fed to a second comparator input of comparator 216 by a block 215. The fixed value output by block 215 may be user configurable or hardwired, to give some examples.

In the embodiment of FIG. 21, comparator 216 has two outputs, a first output which is activated when the value output by counter 213 exceeds the value output by block 215, which corresponds to a situation where a frequency f of first oscillator 212 is greater than a frequency $f_0$ as represented by the value output by block 215, and a second output which is activated when f is smaller or equal to $f_0$. The first output may also be omitted in some embodiments. The second output controls an NMOS transistor 210 which may be coupled between an output line 211 and ground. Output line 211 may for example be an output line of a circuit providing redundancy.

In this case, when the frequency f falls below $f_0$, NMOS transistor 210 pulls a signal at line 211 towards ground, similar to the way NMOS transistor NMOS2 of dependency breaking structure 143 of FIG. 14 pulls an output of second circuit 141 towards ground. In the embodiment of FIG. 21, a falling frequency may for example be associated with increasing humidity, and f falling below $f_0$ may indicate that the humidity has left a specified range.

In some embodiments, the first output additionally may be coupled to a PMOS transistor 217 coupled between a positive supply voltage 218 and a line 219. Line 219 may be an output line of a further circuit providing redundancy. When the frequency f falls below $f_0$, the first output of comparator 216 is low and therefore PMOS transistor 217 becomes conducting. Therefore, a signal on line 219 is pulled towards positive supply voltage 218. In this way, an opposite behavior may be achieved on lines 211, 219 when a humidity leaves a specified range.

In other embodiments, NMOS transistor 210 and PMOS transistor 217 may be omitted, and the output(s) of comparator 216 may be directly evaluated (which for example would correspond to a situation where the dependency breaking structure of FIG. 21 has its own output, as for example shown in the embodiment of FIG. 13).

Furthermore, instead of implementing first oscillator circuit 212 as shown in FIG. 20A, in other embodiments first oscillator circuit 212 may be implemented as shown in FIG. 20B, and the evaluation logic controlling NMOS transistor 210 and/or PMOS transistor 217 may be reversed. This reversal may for example be achieved by coupling NMOS transistor 210 with the first output of comparator 216 ($f>f_0$), and coupling PMOS transistor 217 with the second output ($f<=f_0$) of comparator 216.

In yet other embodiments, two dependency breaking structures as shown in FIG. 21 may be used, one utilizing an oscillator as shown in FIG. 20A as first oscillator 212 and the other one utilizing an oscillator as shown in FIG. 20B as first oscillator 212. In such an embodiment, for the detection of the disturbance parameter humidity two structures with opposite behavior (The oscillators of FIGS. 20A and 20B) are used.

Figure 22:
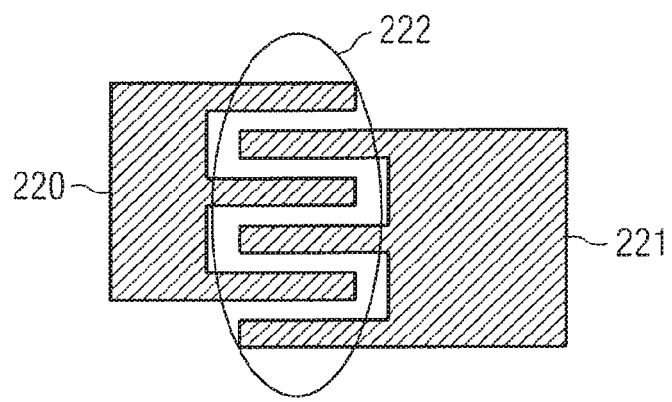
FIG. 22 shows a resistor usable in some embodiments.

A further possibility to detect humidity besides a varying capacitance is to use a varying resistance. In FIG. 22, an example for a variable resistor according to an embodiment is shown. The resistor of FIG. 22 comprises a first comb-shaped electrode 220 and a second comb-shaped electrode 221 which may be manufactured by a planar semiconductor process in some embodiments, for example in a metallization layer or a polysilicon layer. The "teeth" of the comb-shaped electrodes 220, 221 are arranged in an interleaving manner as shown in FIG. 22. When humidity enters an area 222 between the "teeth", a resistance value between electrodes 221, 220 changes, for example decreases. This may be used to provide dependency breaking structures sensitive to humidity.

For example, in the embodiment of FIG. 14 or 16 in the voltage dividers transistors T1, T2 (which essentially provide a variable resistance in response to disturbance parameter like stress, carriers in the substrate or temperature) may be replaced by resistor structures as shown in FIG. 22 (which provide a variable resistance in response to humidity). The associated resistances R1, R2 of the voltage divider then may be dimensioned accordingly to yield a desired result, for example be provided with a high resistance value (high ohmic resistance).

With these modifications, the dependency breaking structures of FIGS. 14 and 16 may be used to detect a humidity being outside a specified range.

In the embodiment discussed so far with reference to FIGS. 10-22, dependency breaking structures are provided separately to circuits performing the actual desired function. In other embodiments, redundant circuits themselves may be modified to have a desired dependency breaking effect. This will be explained using a further illustrative embodiment with reference to FIGS. 23 and 24.

Figure 23:
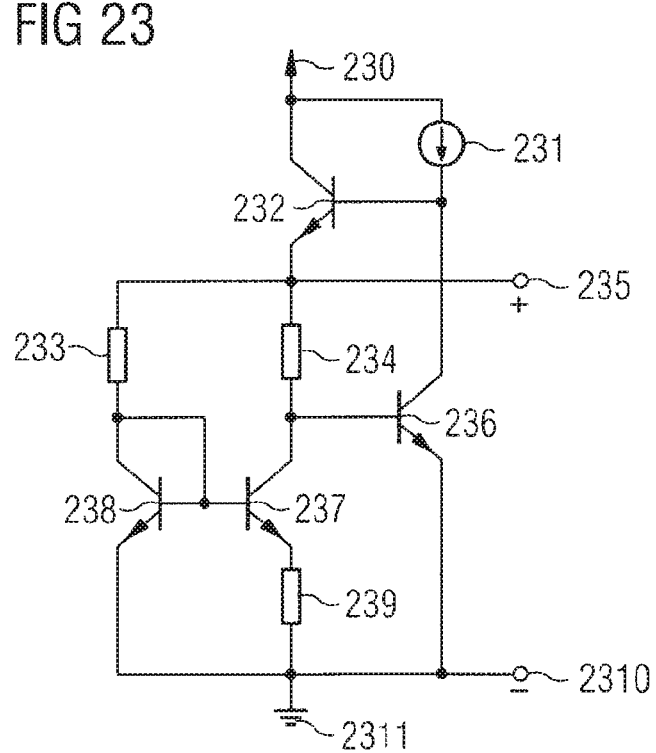
FIG. 23 illustrates a bandgap reference circuit usable in some embodiments.

In FIG. 23, a bandgap circuit is shown which outputs a reference voltage between output terminals 235 and 2310. 230 denotes a positive supply voltage, and 2311 denotes ground. The bandgap reference circuit of FIG. 23 comprises transistors 232, 236, 237 and 238, resistors 233, 234 and 239 as well as a current source 231. The circuit of FIG. 23 per se is a conventional bandgap reference circuit and is also referred to as Widlar bandgap reference circuit.

Figure 24:
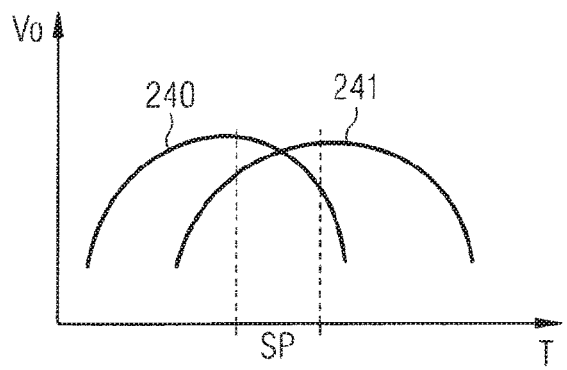
FIG. 24 illustrates the behavior of two bandgap reference circuits according to an embodiment.

The output value of such a circuit depends to some extent on a temperature of the circuit, such that temperature is a disturbance parameter for the circuit of FIG. 23. In embodiments, two bandgap reference circuits may be provided for example as first circuit 11 and second circuit 12 of the embodiment of FIG. 1 to provide a reference voltage with redundancy. Furthermore, in an embodiment, the two bandgap reference circuits are detuned with respect to each other such that outside a specified range of the disturbance parameter (e.g. temperature) they produce significantly different results. Such a detuning may for example be performed by changing the transistor design or by changing resistance values. In some embodiments, this may lead to a behavior as shown in FIG. 24. In FIG. 24, a first curve 240 for example shows an output voltage versus temperature for a first bandgap reference circuit as shown in FIG. 23, and a second curve 241 shows the output voltage versus temperature for a second bandgap reference circuit as shown in FIG. 23, the second bandgap reference circuit being detuned with respect to the first bandgap reference circuit. As can be seen in FIG. 24, the difference between the two curves 240, 241 in a specified range SP is comparatively small, for example within an acceptable tolerance for the reference voltage.

Outside the specified range SP, the difference between curves 240 and 241 becomes greater. Therefore, for example by comparing the difference between the outputs of the two bandgap reference circuits with a threshold, the temperature leaving the specified range SP may be detected. Such a detection may be performed by an internal or external circuit, as generally discussed with reference to FIGS. 14 and 16.

It should be noted that in case of the embodiment of FIG. 24 at least in some area the difference between curves 240, 241 increases as the distance between temperature and the specified range SP increases as soon as the temperature is outside the specified range SP, which may ensure a reliable detection of the temperature leaving the specified range in some embodiments. In embodiments, in other areas or ranges, for example far away from the specified range SP, this need not be the case. In some embodiments, the two bandgap reference circuits are designed such that the area where the difference between curves 240, 241 increases as the distance between temperature and the specified range SP increases is made large to ensure reliable detection of the disturbance parameter leaving the specified range SP.

It should be noted that the bandgap reference circuit in FIG. 23 is merely to be taken as an example, and generally the approach of detuning two circuits from each other may be taken in case a difference between outputs of the two circuits may be kept within an acceptable tolerance within a specified range while the difference increases outside the specified range, as illustratively shown in FIG. 24.

Next, with reference to FIGS. 25 and 26 methods according to embodiments will be discussed in detail. While these methods are illustrated as a series of acts or events, the order in which these acts or events are illustrated is not to be construed as limiting.

Figure 25:
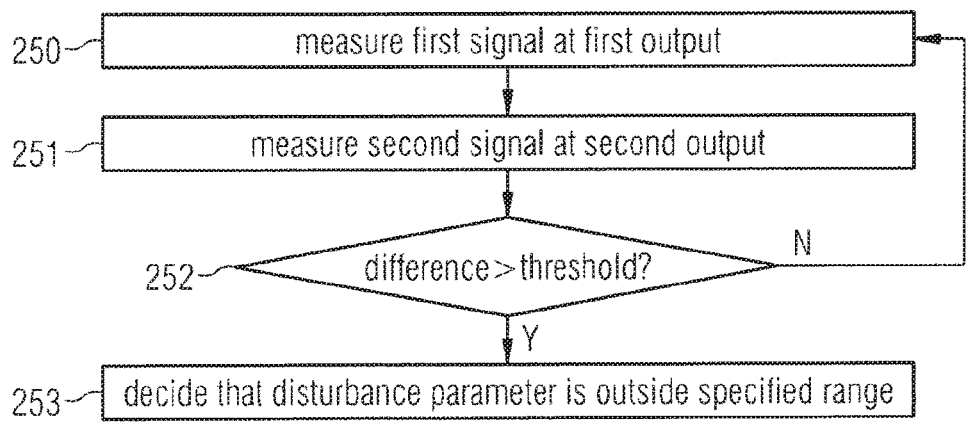
FIG. 25 is a flowchart illustrating a method according to an embodiment.

In FIG. 25, an embodiment of a method is shown which may for example be used in conjunction with circuits where two outputs show a diverging behavior when a disturbance parameter leaves a specified range, for example using the circuits of FIGS. 1, 10, 11, 12, 14, 17, 21 or as explained with reference to FIG. 23. However, use of the method of FIG. 25 is not limited to the afore-mentioned circuits and devices.

At 250, a first signal at a first output of a circuit is measured, for example at a first output coupled with a dependency breaking structure or a first output coupled with a circuit detuned with respect to a further circuit. At 251, a second signal at a second output is measured, for example a second output coupled with a further dependency breaking structure, an output without dependency breaking structure or an output coupled with the above-mentioned further circuit detuned with respect to the circuit.

At 252, it is evaluated if a difference between a property of the first signal and a property of the second signal exceeds a predetermined threshold. Properties may for example include voltage, current, duty cycle, frequency or pulse form, just to give a few examples. At 253, if the difference exceeds the threshold, the method decides that the disturbance parameter is outside a specified range. Based on this decision, measures may be taken like issuing a warning, deactivating a function, shutting down a function or any other appropriate measure.

In case the difference does not exceed the threshold at 252, in embodiments the method may continue at 250 to provide a continuous monitoring. In other embodiments, the method may be performed for example in regular or irregular intervals.

Figure 26:
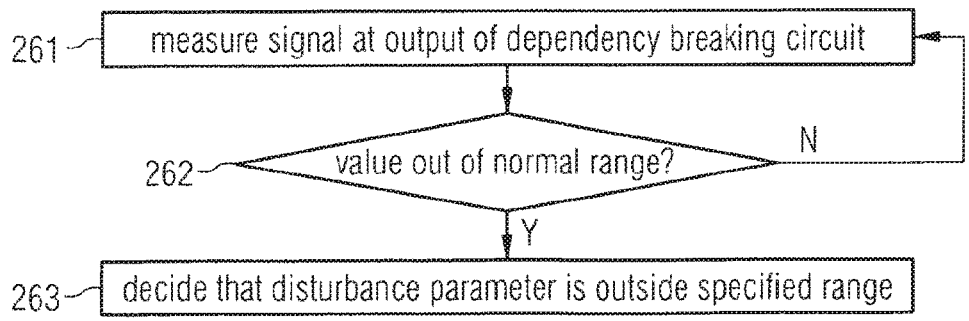
FIG. 26 is a flowchart illustrating a method according to a further embodiment.

In FIG. 26, a method according to a further embodiment is schematically shown. At 261, a signal at an output of a dependency breaking structure is measured. For example, an output of dependency breaking structure 132 of FIG. 13 or an output of evaluation circuit 165 may be measured.

At 262, it is evaluated, if a value or property of the measured signal is outside a normal range, i.e. outside a range corresponding to a specified range of a disturbance parameter. If this is the case, at 263 it is decided that the disturbance parameter is outside the specified disturbance parameter range, and again appropriate measures may be taken. In case the value or the property of the measured signal is within the normal range, the method may continue at 261 to provide a continuous monitoring. In other embodiments, the method may be performed periodically or in non-periodic intervals.

While a plurality of different embodiments has been described, these embodiments are not to be construed as limiting. For example, redundant circuits like the circuits described with reference to the figures may be used to perform any desired function needed in a particular application. As employment of the techniques and approaches described herein for detection of a disturbance parameter being outside a specified range does not depend on the exact functioning of the circuits, the techniques are applicable to essentially any desired kinds of circuit.

Moreover, in embodiments where dependency breaking circuits are directly evaluated (for example the embodiments of FIGS. 12, 13 and 16), instead of two redundant circuits which, when operating properly yield essentially the same output signal, also a first circuit for performing a specific function and a second circuit monitoring the correct functioning of the first circuit may be used. Redundant circuits may have the same design, or may have different designs for performing the same function (for example different kinds of analog to digital converters). Moreover, while two redundant circuits have been described in embodiments for ease of representation, also more than two redundant circuits may be used. In such cases, for example one of the redundant circuits, two of the redundant circuits or more of two of the redundant circuits may have dependency breaking structures associated therewith and/or may be detuned from each other.

Therefore, as evident from the above explanations, various modifications and variations are possible without departing from the scope of the present application.

The invention claimed is:

1. A dependency breaking circuit, comprising:
a sensing element sensitive to at least one disturbance parameter,
an output coupled with the sensing element, a signal at the output being dependent on the at least one disturbance parameter such that a fault condition is detected if the disturbance parameter is outside a specified range, and
a transistor coupled between a reference potential and the output, a control input of the transistor being coupled with the sensing element.

2. The circuit of claim 1, wherein the sensing element comprises a voltage divider, the voltage divider comprising a component comprising an impedance of which is sensitive to the disturbance parameter.

3. The circuit of claim 2, wherein the component is selected from a group consisting of a resistor and a transistor.

4. The circuit of claim 1, wherein the sensing element comprises an oscillator, the oscillator being sensitive to a variation of the disturbance parameter.

5. The circuit of claim 4, wherein the oscillator comprises a capacitor sensitive to humidity.

6. The circuit of claim 1, wherein the sensing element comprises an antenna.

7. The circuit of claim 1, wherein the disturbance parameter comprises at least one parameter selected from the group consisting of mechanical stress, carriers in a substrate, electromagnetic radiation, humidity, particle radiation, or temperature.

8. A functional safety device, comprising:
a first dependency breaking circuit, comprising:
a first sensing element sensitive to at least one disturbance parameter, and
a first output coupled with the first sensing element, a signal at the first output being dependent on the at least one disturbance parameter such that a fault condition is detected if the at least one disturbance parameter is outside a specified range; and
a second dependency breaking circuit, comprising:
a second sensing element sensitive to the at least one disturbance parameter, and
a second output coupled with the second sensing element, a signal at the second output being dependent on the at least one disturbance parameter such that a fault condition is detected if the at least one disturbance parameter is outside the specified range,
wherein a first response of the signal at the first output of the first dependency breaking circuit when the at least one disturbance parameter leaves the specified range differs from a second response of the signal at the second output of the second dependency breaking circuit when the at least one disturbance parameter leaves the specified range.

9. A functional safety device, comprising:
a first circuit to provide a predetermined functionality, and
a second circuit to provide the predetermined functionality to provide redundancy, and
a dependency breaking circuit, comprising:
a sensing element sensitive to at least one disturbance parameter, and an output coupled with the sensing element, a signal at the output being dependent on the at least one disturbance parameter such that a fault condition is detected if the at least one disturbance parameter is outside a specified range,
wherein the dependency breaking circuit is coupled with the first circuit to modify an output of the first circuit when the at least one disturbance parameter is outside the specified range.

10. The device of claim 8, wherein the first response has a first slope, and the second response has a second slope different from the first slope.

11. The device of claim 10, wherein a sign of the first slope differs from a sign of the second slope.

12. The device of claim 8, wherein the first response comprises a pulling towards a first signal level, and the second response comprises a pulling towards a second signal level different from the first signal level.

13. The device of claim 12, wherein the first signal level is a first voltage potential, and the second signal level is a second voltage potential different from the first voltage potential.

14. The device of claim 8, wherein the first dependency breaking circuit and the second dependency breaking circuit are implemented on a single substrate.

15. The device of claim 8, further comprising an evaluation circuit, the evaluation circuit being responsive to a difference between the signal at the output of the first dependency breaking circuit and the signal at the output of the second dependency breaking circuit.

16. The device of claim 8, further comprising:
a first circuit to provide a predetermined functionality, and
a second circuit to provide the predetermined functionality to provide redundancy.

17. The device of claim 16,
wherein the first dependency breaking circuit is coupled with the first circuit to modify an output of the first circuit when the at least one disturbance parameter is outside the specified range, and
wherein the second dependency breaking circuit is coupled with the second circuit to modify an output of the second circuit when the at least one disturbance parameter is outside the specified range, a modification of the output of the first circuit being different from a modification of the output of the second circuit.

18. The device of claim 9, wherein the first circuit and the second circuit are provided on a single substrate.

19. The device of claim 9,
wherein the first circuit has a substantially identical circuit design as the second circuit.

20. A functional safety device, comprising:
a first circuit to provide a predetermined functionality when at least one disturbance parameter is within a specified range, and
a second circuit to provide the predetermined functionality when the at least one disturbance parameter is within the specified range to provide redundancy, wherein the first circuit is detuned with respect to the second circuit to cause a first signal of the first circuit to deviate from a second signal of the second circuit by more than a predetermined tolerance when the at least one disturbance parameter is outside the specified range.

21. The device of claim 20, wherein the first circuit comprises a bandgap reference circuit, and wherein the second circuit comprises a bandgap reference circuit detuned with respect to the first bandgap reference circuit.

22. The device of claim 20, wherein the first circuit has a substantially identical circuit design as the second circuit, wherein components of the first circuit are modified compared to the second circuit to provide the detuning.

23. A method, comprising:
measuring a first signal at a first output of a circuit on a substrate, the circuit being sensitive to at least one disturbance parameter,
measuring a second signal at a second output of the circuit, and
deciding that the at least one disturbance parameter is outside a specified range, if a property of the first signal differs from the property of the second signal by more than a predetermined tolerance, wherein the circuit comprises:
a first dependency breaking circuit, comprising:
a first sensing element sensitive to at least one disturbance parameter, and
a first output coupled with the first sensing element, a signal at the first output being dependent on the at least one disturbance parameter such that a fault condition is detected if the at least one disturbance parameter is outside a specified range; and
a second dependency breaking circuit, comprising:
a second sensing element sensitive to the at least one disturbance parameter, and
a second output coupled with the second sensing element, a signal at the second output being dependent on the at least one disturbance parameter such that a fault condition is detected if the at least one disturbance parameter is outside a specified range,
wherein a first response of the signal at the first output of the first dependency breaking circuit when the at least one disturbance parameter leaves the specified range differs from a second response of the signal at the second output of the second dependency breaking circuit when the at least one disturbance parameter leaves the specified range,
wherein the first output of the circuit is coupled to the first output of the first dependency breaking circuit, and the second output of the circuit is coupled to the second output of the second dependency breaking circuit.

24. A method, comprising:
measuring a first signal at a first output of a circuit on a substrate, the circuit being sensitive to at least one disturbance parameter,
measuring a second signal at a second output of the circuit, and
deciding that the at least one disturbance parameter is outside a specified range, if a property of the first signal differs from the property of the second signal by more than a predetermined tolerance, wherein the circuit comprises:
a first circuit to provide a predetermined functionality, and
a second circuit to provide the predetermined functionality to provide redundancy, and
a dependency breaking circuit, comprising:
a sensing element sensitive to the at least one disturbance parameter, and an output coupled with the sensing element, a signal at the output being dependent on the at least one disturbance parameter such that a fault condition is detected if the at least one disturbance parameter is outside a specified range,
wherein the dependency breaking circuit is coupled with the first circuit to modify an output of the first circuit when the at least one disturbance parameter is outside the specified range,
wherein the first output of the circuit is coupled to an output of the first circuit, and the second output of the circuit is coupled to an output of the second circuit.

25. The method of claim 23,
wherein the property is selected from a group consisting of a voltage, a current, a duty cycle, a frequency or a pulse form.

* * * * *

UNITED STATES PATENT AND TRADEMARK OFFICE
CERTIFICATE OF CORRECTION

PATENT NO. : 10,229,805 B2
APPLICATION NO. : 15/240544
DATED : March 12, 2019
INVENTOR(S) : Zettler et al.

Page 1 of 1

It is certified that error appears in the above-identified patent and that said Letters Patent is hereby corrected as shown below:

On the Title Page

Item (63): Replace "Related U.S. Application Data" from "Continuation of Application PCT/EP2014/053214 filed on Feb. 9, 2014." with -- Continuation of Application PCT/EP2014/053214 filed on Feb. 19, 2014. --

Signed and Sealed this
Twenty-first Day of May, 2019

Andrei Iancu
*Director of the United States Patent and Trademark Office*